United States Patent [19]
Walker, Jr.

[11] Patent Number: 5,224,502
[45] Date of Patent: Jul. 6, 1993

[54] HAND-HOLDABLE DENTAL FLOSSING DEVICE AND METHOD

[76] Inventor: Myles M. Walker, Jr., 616 Santa Clara Ave., Alameda, Calif. 94501

[21] Appl. No.: 756,291

[22] Filed: Sep. 6, 1991

Related U.S. Application Data

[63] Continuation-in-part of Ser. No. 498,538, Mar. 26, 1990, abandoned.

[51] Int. Cl.$^5$ ............................................. A61C 15/00
[52] U.S. Cl. .................................. 132/325; 132/324; 132/326
[58] Field of Search ............... 132/323, 324, 325, 326, 132/328

[56] References Cited

U.S. PATENT DOCUMENTS

| | | | |
|---|---|---|---|
| 1,274,423 | 8/1918 | Kristmann | 132/324 |
| 3,799,177 | 3/1974 | Bragg | 132/326 |
| 3,804,102 | 4/1974 | Bennington | 132/321 |
| 4,022,229 | 5/1977 | Minka | 132/326 |
| 4,655,234 | 4/1987 | Bowden | 132/325 |
| 4,657,034 | 4/1987 | Koski | 132/324 |
| 4,920,993 | 5/1990 | Mackie | 132/324 |

Primary Examiner—Gene Mancene
Assistant Examiner—Cindy A. Cherichetti
Attorney, Agent, or Firm—Thomas J. Perkowski

[57] ABSTRACT

A hand-holdable flossing device is provided for dispensing and supporting a selected length of dispensed dental floss for use in an operational position within an oral cavity. In general, the flossing device has a front end and a rear end, and an elongated gripping surface extending therebetween for encirclement within a user's hand. The handle portion has a hollow cavity for containing a supply of dental floss, and a passageway formed in the front end and in communication with the hollow cavity to permit passage of dental floss from the hollow cavity through the passageway. The dispensing portion has a base portion operably associated with an elongated portion which extends in an essentially linear direction and terminates in a tip portion. The base portion, elongated portion and tip portion has a continuously extending dispenser bore formed therethrough which permits dental floss to slidably pass from the passageway through the base portion and said elongated portion and exit from the tip portion. Dispensing portion can be operably connected to the handle portion in a variety of ways, including a bayonet-type or screw-thread type interconnection, each of which permits rotatable arrangement of the dispensing and handle portions into a floss locking configuration and a floss releasing configuration. In both embodiments, a selected length of dental floss is permitted to be pulled through said dispenser bore and dispensed from the tip portion when the handle portion and the dispenser portion are rotatably arranged into the floss releasing configuration. Also, the selected length of dispensed dental floss is locked and restrained from being pulled through the dispenser bore when the handle portion and the dispensing portion are rotatably arranged into the floss locking configuration.

4 Claims, 4 Drawing Sheets

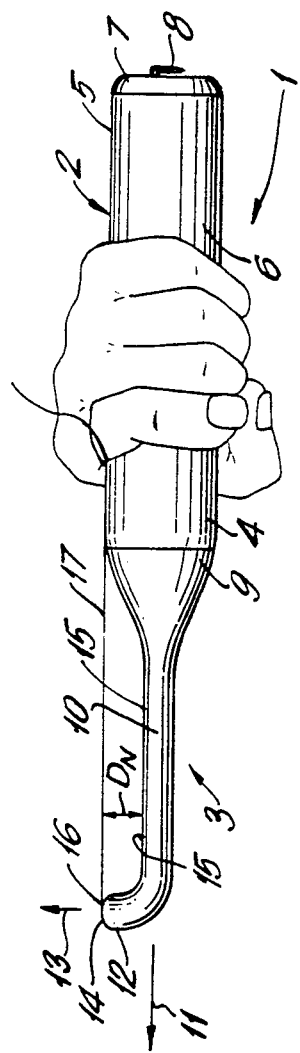
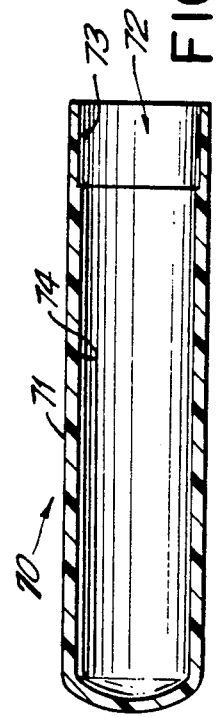
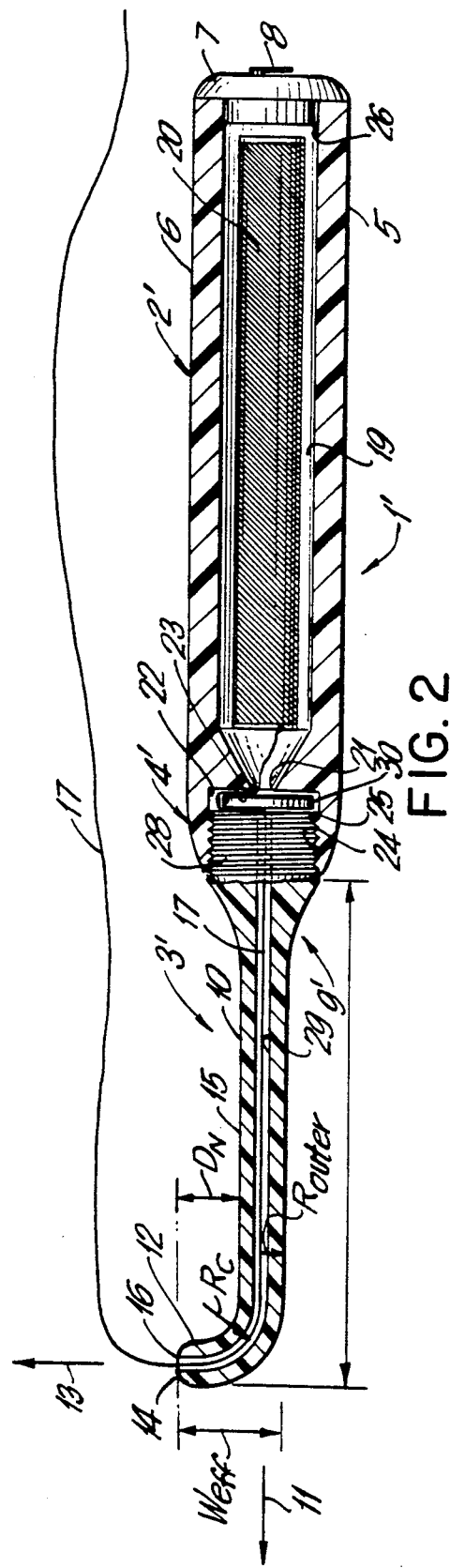
FIG. 1
FIG. 1A
FIG. 2

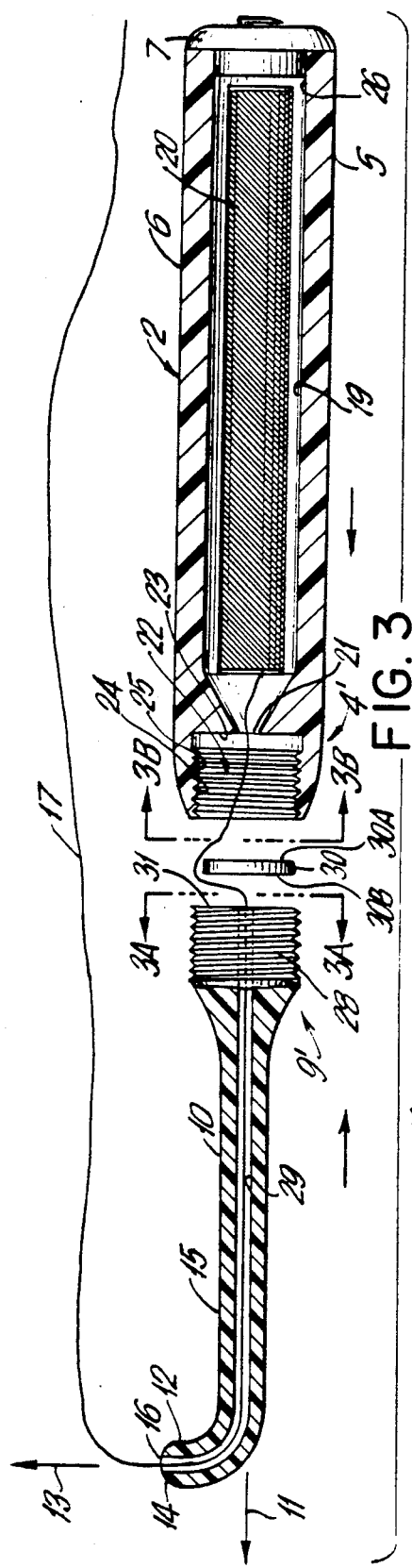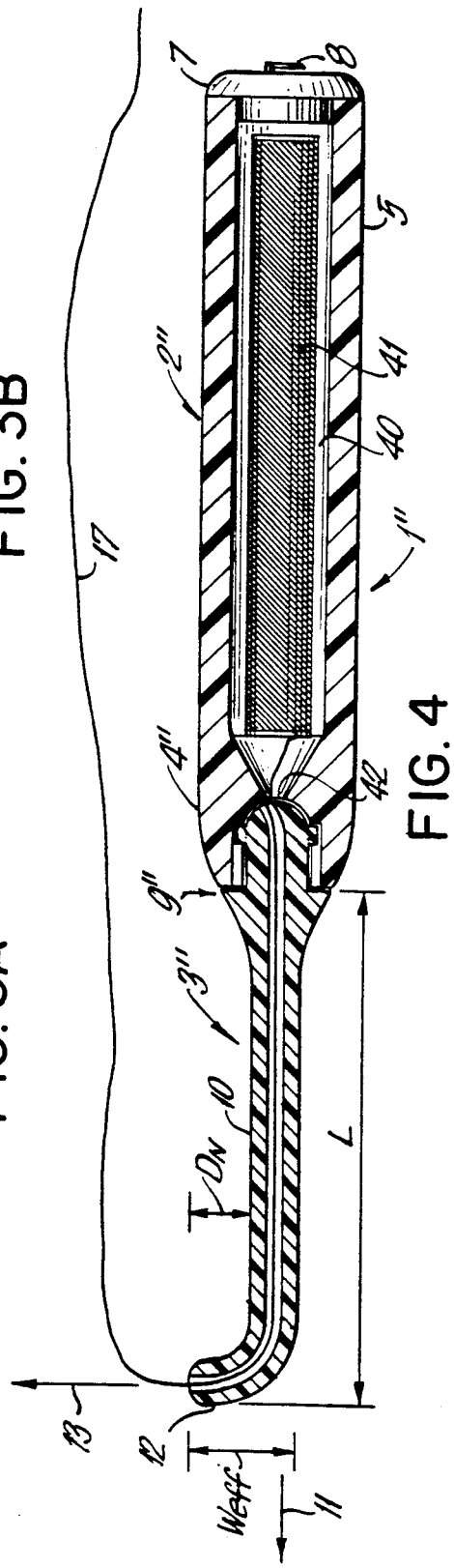
FIG. 3
FIG. 3A
FIG. 3B
FIG. 4

HAND-HOLDABLE DENTAL FLOSSING DEVICE AND METHOD

This is a continuation-in-part application of copending application Ser. No. 07/498,538 entitled "Flossing Tool," filed on Mar. 26, 1990 now abandoned.

BACKGROUND OF THE INVENTION

1. Field of Invention

The present invention relates generally to hand-holdable dental flossing devices and methods of flossing teeth using the same. More particularly, however, the present invention relates to a hand-holdable device which permits dispensing of a selected length of dental floss which can be selectively restrained internally and tautly supported by the device at one end and by at least one digit of the user's hand at the other end, in order to operationally position a portion of the tautly supported dental floss in the user's oral cavity for safe and effective flossing of teeth using only a single hand.

2. Brief Description of the Prior Art

The importance of flossing as part of daily dental care has become greatly appreciated over the years. Consequently, a variety of dental floss dispensing and support devices have been proposed.

Floss dispensing and support devices representative of the prior art can be found in U.S. Pat. No. 4,920,993 to Mackie; U.S. Pat. No. 4,342,324 to Sanderson; U.S. Pat. No. 4,655,234 to Bowden; 3,949,769 to Minka; U.S. Pat. No. 3,908,678 to Conn et al.; U.S. Pat. No. 3,814,114 to Roberts; U.S. Pat. No. 3,804,102 to Bennington; U.S. Pat. No. 3,799,177 to Bragg; U.S. Pat. No. 1,780,045 to Schubert; and U.S. Pat. No. 911,664 to Loure. While each of these prior art devices contain, dispense and support dental floss in one way or another, they nevertheless suffer from a number of significant shortcomings and drawbacks.

In particular, such prior art devices are restrictive in the manipulative sense, and thus awkward to use. They fail to protect the gums from injury. They do not permit easy disengagement or repositioning upon breaking or sticking of floss between teeth. They do not permit simple releasing and locking of dental floss. Also, they fail to fully exploit the strength, flexibility, and dexterity affordable by the human hand.

OBJECTS OF THE INVENTION

Accordingly, it is a primary object of the present invention to provide a dental flossing device which overcomes the shortcomings and drawbacks of the prior art while providing a number of significant advantages.

It is a further object of the present invention to provide a hand-holdable dental flossing device which contains a supply of dental floss in a sanitary condition, and permits dispensing a selected length of dental floss and selective internal engagement thereof to essentially fix the dental floss at one end, while permitting wrapping of the free end thereof about a user's finger so that when the device is grasped within the user's hand, the selected length is held taut for flossing operations.

Another object of the present invention is to provide such a hand-holdable dental flossing device, in which its dispensing portion has a tip that is configured to safely stop unintentional advancement of the dispensing portion into the oral cavity, while protecting the gums and other soft oral tissues.

Another object of the present invention is to provide such a hand-holdable dental flossing tool, in which the handle portion contains a supply of dental floss that is dispensed through the connected dispensing portion and release and locking of dental floss within the device is effected by simply rotating the dispensing portion relative to the handle portion.

Another object of the present invention is to provide such a hand-holdable dental flossing tool, in which dispensing portion is protected within a removable cover portion when not being used, and in which the cover portion can be removed and connected to the rear end of the handle portion during flossing operations, to improve the mechanical advantage of the device.

An even further object of the present invention is to provide such a hand-holdable dental flossing device, in which the tip portion is orthodontically correct and minimizes the length of the dispensing portion that must be introduced into the oral cavity during flossing operations.

These and other objects of the present invention will become apparent hereinafter.

SUMMARY OF THE INVENTION

According to one of the general aspects of the present invention, a hand-holdable flossing device is provided for dispensing and supporting a selected length of dispensed dent floss for use in an operational flossing position within an oral cavity.

In general, the flossing device has a front end and a rear end, and an elongated gripping surface extending therebetween for encirclement within a user's hand. The handle portion has a hollow cavity for containing a supply of dental floss. A passageway is formed in the front end of the handle portion and is communication with the hollow cavity to permit passage of dental floss from the hollow cavity through the passageway.

The dispensing portion is releasably connect to the front end of the handle portion and has a base portion operably associated with an elongated portion which extends in an essentially linear direction and terminates in a tip portion which deflects orthogonally away from the linear direction. The base portion, elongated portion and tip portion have a continuously extending dispenser bore formed therethrough which permits dental floss to slidably pass from the passageway through the base portion and said elongated portion and exit from the tip portion.

In a first embodiment of the invention, the dispensing portion is operably connected to the handle portion by way of a bayonet-type interconnection which permits rotatable arrangement of the dispensing and handle portions into a floss locking configuration and a floss releasing configuration. In a second embodiment of the invention, the handle portion is operably connected to the handle portion by a screw-thread type interconnection which permits rotatable arrangement of the dispensing and handle portions into a floss locking configuration and a floss releasing configuration. In either embodiment, a selected length of dental floss is permitted to be pulled through the dispenser bore and dispensed from the tip portion when the handle portion and the dispenser portion are rotatably arranged into the floss releasing configuration. Also, the selected length of dispensed dental floss is locked and restrained from being pulled through the dispenser bore when the handle portion and the dispensing portion are rotatably arranged into the floss locking configuration.

According to another aspect of the present invention, a method of flossing is provided using the flossing device of the present invention.

BRIEF DESCRIPTION OF THE DRAWINGS

For a more complete understanding of the present invention, the Detailed Description of the Illustrated Embodiments is to be taken in connection with the drawings, in which:

FIG. 1 is a perspective view of the dental flossing device of the present invention, shown grasped within a person's hand;

FIG. 1A is a cross-sectional longitudinal view of the cover portion of the flossing device of the present invention;

FIG. 2 is an elevated cross-sectional view taken along the longitudinal axis of the dental flossing device of the first embodiment of the present invention;

FIG. 3 is an exploded cross-sectional view taken along the longitudinal axis of the dental flossing device of FIG. 2;

FIG. 3A is an elevated end view taken along line 3A—3A of FIG. 3, showing the dispensing portion of the dental flossing device of the first embodiment of the present invention;

FIG. 3B is an elevated end view taken along line 3B—3B of FIG. 3, showing the handle portion of the dental flossing de of the first embodiment of the present invention;

FIG. 4 is an elevated cross-sectional view taken along the longitudinal axis of the dental flossing device of the second embodiment of the present invention;

FIG. 5A is an elevated end view taken along line 5A—5A of FIG. 5, showing the dispensing portion of the dental flossing device of the second embodiment of the present invention;

FIG. 5B is an elevated end view taken along line 5B—5B of FIG. 5, showing the handle portion of the dental flossing device of the second embodiment of the present invention;

FIG. 5C is a cross-sectional view taken along line 5C—5C of FIG. 5, showing the front end of the handle portion of the dental flossing device of the second embodiment of the present invention;

FIG. 5D is a cross-sectional view taken along line 5D—5D of FIG. 5, showing the front end of the handle portion of the dental flossing device of the second embodiment of the present invention; FIG. 5;

DETAILED DESCRIPTION OF THE ILLUSTRATED EMBODIMENTS

Figure 5:
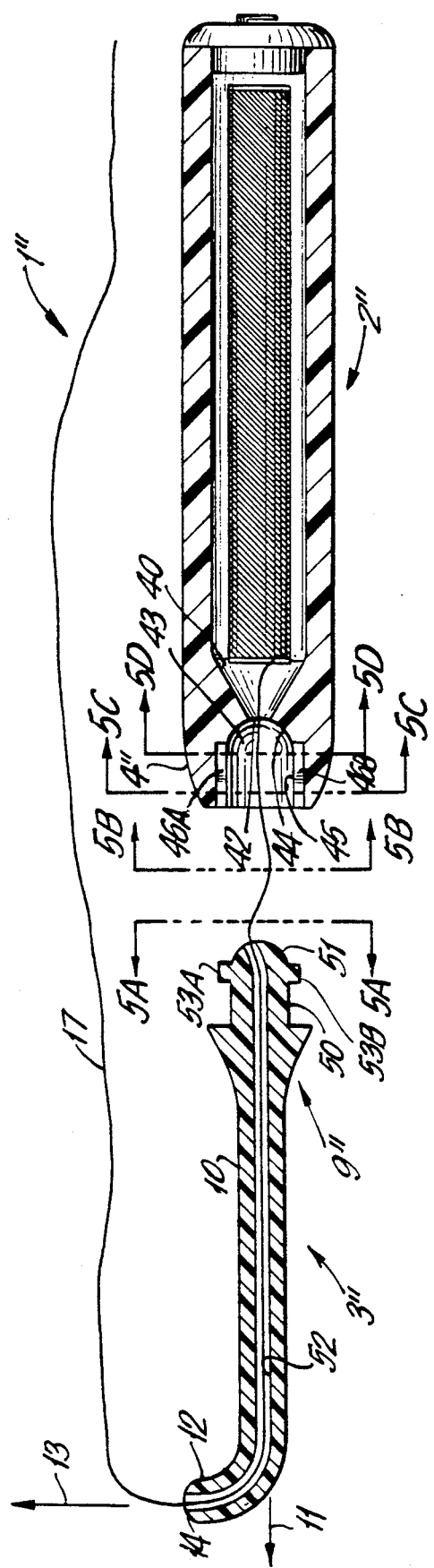
FIG. 5 is an exploded cross-sectional view taken along the longitudinal axis of the dental flossing device of the second embodiment of the present invention.

As illustrated in FIG. 1, the dental flossing device of the present invention is shown grasped within a user's hand. In general, dental flossing device 1 comprises a handle portion 2 and a floss dispensing portion 3.

As shown, handle portion 2 has a front end 4 and a rear end 5, and an elongated gripping surface 6 extending therebetween. In the illustrated embodiments, elongated gripping surface 6 is generally cylindrical in geometry, although such a gross geometry with a slight taper will expectedly perform with similar results. Notably, rear end 5 of the handle portion is adapted to receive an end cap 7 which carries a floss cutting element 8 well known in the art.

Floss dispensing portion 3 has a base portion 9 and a relatively thin, elongated portion 10 which extends from base portion 9 in an essentially linear direction indicated by reference arrow 11. As shown, elongated portion 10 terminates in a tip portion 12 which deflects away from the linear direction and along a final direction 13 which is generally orthogonal to linear direction 11. Significantly, the final direction is achieved through a very small radius of curvature $r_c$. Radius of curvature $r_c$ can be within the range of from 3/16 of an inch to about 7/16 of an inch, and preferably is about 5/16 of an inch. Advantageously, this rapid transition from the linearly extending elongated portion into the tip portion provides a significant increase in the operative flossing length of the dispensing portion. This translates into a major improvement over prior art devices, namely; minimizing the length of the dispensing portion that must be introduced into the oral cavity during flossing operations.

As defined in FIG. 1, the effective width of tip portion $W_{eff}$ is measured from semispherically shaped tip end 16 to the outer diameter $R_{outer}$ of the elongated member, adjacent tip portion 11. The effective width of tip portion can be within the range from about ⅜ of an inch to about 1 inch. The normal distance $D_N$, measured from the tooth guiding surface 15 of the elongated portion to the tip end 16, can be within the range of ¼ of an inch to about ½ of an inch, as this will typically be the range of height from the crown of a tooth to desired depth below the gumline as illustrated in FIG. 8A.

In view of the fact that individual teeth and oral cavities vary in size across the human population, the present invention completes selecting particular values for $W_{eff}$ and $D_N$ which tailor the dimensions of the tip portion to different classes of individuals each being characterized by a particular range of teeth and oral cavity dimensions. In a preferred embodiment, the diameter of the front end of the handle portion will be selected so that, for selected values of $W_{eff}$ and $D_N$, selected length of dental floss 17 exiting from tip end 16 and wrapped about either the user's index finger (or thumb) as shown in FIG. 1, will be disposed essentially parallel to the linear direction of the elongated member of dispensing portion 3.

As illustrated in FIG. 1A, the flossing device 1 also includes cover portion 70 for maintaining the dispensing portion clean when the device is not being used. As shown, cover portion 70 has an essentially cylindrical enclosure 71, having an open end 72 with a cylindrical recess 73 formed in enclosure walls 74. When the device is not being used cover portion 70 can be slid over the dispensing portion and recess 73 snap-fitted over front end 4 of the handle portion. When the flossing device is being used, cover portion 70 is removed from the dispensing portion and open end 72 can be snap fitted onto rear end 5 of the handle portion. Advantageously, after use of the device and severing the length of used dental floss, the fresh length of dental floss can be wrapped about the dispensing portion, and then cover portion 70 snapped thereover for protection until the next use.

As illustrated in FIG. 1, dispensing and handle portions 3 and 2 are operably connected along the longitudinal extent of these portions. Two specific ways in which such operational connections can be effected, are illustrated in the first and second embodiments of the present invention, shown in FIGS. 2 through 3B, and FIGS. 4 through 5D, respectively.

Figure 6:
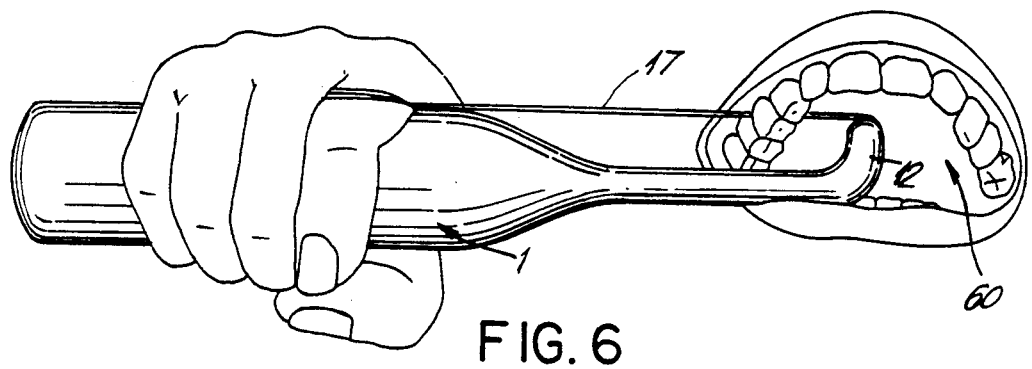
FIG. 6 is a perspective, partially fragmented, view of an oral cavity having a set of teeth shown being flossed with a tautly held length of dental floss supported in a first operational position within the oral cavity, between the tip portion of the dental flossing device hereof and the user's hand gripping the same.
Figure 7:
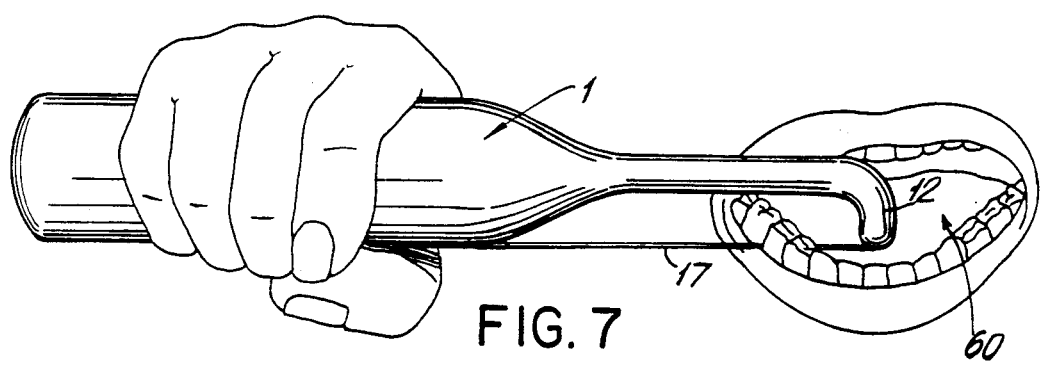
FIG. 7 is a perspective, partially fragmented view of an oral cavity having a set of teeth shown being flossed with a tautly held length of dental floss supported in a second operational position within the oral cavity, between the tip portion of the dental flossing device hereof and the user's hand gripping the same.

Referring to FIGS. 2 through 3B, the details of the first embodiment of the present invention, will now be described. In general, this embodiment is characterized by a screw-thread type interconnection which permits rotatable arrangement of the dispensing and handle portions into a floss locking configuration and a floss releasing configuration. When the handle and dispensing portions are rotatably arranged into the floss releasing configuration, a selected length of dental is permitted to be pulled through the tip end of the dispensing portion and out from within the interior cavity of the handle portion, where a supply of dental floss is contained. When handle and dispensing portions are arranged into the flossing locking configuration, the selected length is internally locked and restrained from being pulled through the dispenser bore. When drawn out dental floss is severed at floss cutter element 8, the distance between the outer surface of tip portion 12 and floss cutter element 8 ensures that each dispensed piece of sanitized dental floss has a uniform length which is suitable for wrapping a number of times about one of the user's digits (e.g. fingers, or thumb) as shown in FIGS. 1, 6 and 7, in particular.

As illustrated in FIG. 2, the first embodiment of the dental flossing device 1' comprises dispensing and handle portions 3' and 2', having essentially all of the external structural features of device 1 shown in FIG. 1. However, the view in FIG. 2 reveals that dental flossing device 1' has a number of internal structural features not shown in FIG. 1.

In particular, handle portion 2' has a hollow cavity 19 for containing a supply of dental floss 20, and also a passageway or channel 21 formed in front end 4'. As shown, passageway 21 is in communication with hollow cavity 19 in order to permit passage of dental floss 17 from hollow cavity 19, through passageway 21 into cylindrical recess 22 formed in the front end of the handle portion. As shown, passageway 21 passes through bottom recess surface 23 and side wall surfaces 24 of recess 22 bear threads 25. The rear end of the handle portion is provided with an access opening 26 for replenishing the supply of dental floss when depleted. End cap 7 described above is insertable into access opening 26 and can be removed to replenish dental floss supply 20 when exhausted.

Dispensing portion 3' has a cylindrically shaped base portion 9' bearing threads 28 which are matched for screw-type engagement with threads 25 on cylindrical side walls of the front end recess of the handle portion. As shown, cylindrical base portion 9' gradually extends into a cylindrically shaped elongated portion 10, having a narrow diameter which will vary in accordance with selected values of $W_{eff}$ and $D_N$, as discussed above. At the distal end of the dispensing portion, elongated portion 10 is bent essentially orthogonally to the longitudinal extent thereof, to form tip portion 12 having a semispherical end tip 14, as hereinbefore described. As illustrated in FIG. 3, base portion 9, elongated member 10 and tip portion 12 have a continuously extending dispenser bore 29 formed therethrough. As shown in FIGS. 2 and 3, dispenser bore 29 permits dental floss to slidably pass from passageway 21 in the handle portion through the base portion, elongated portion and tip portion, and exit from tip end 16.

As illustrated in FIG. 3, dental flossing device 1' of the first embodiment of the present invention, includes a flossing engaging element 3 which is adapted for placement within cylindrical recess 22. In the illustrated embodiment, floss engaging element 30 has a disc-like geometry having first and second planar engaging surfaces 30A and 30B. When the dispensing portion is threaded into the front end recess of the handle portion, as shown in FIG. 2, planar engaging surfaces 30A and 30B are positionable against bottom wall surface 22 of the front end recess, and against bottom wall surface 31 of the base portion, respectively. In this floss locking configuration, dental floss 17 passing through passageway 21 and dispenser bore 29 is securely engaged between (i) bottom wall surface 22 and engaging surface 30A, and (ii) bottom wall surface 31 and engaging surface 30B. Consequently, the floss is internally restrained from being pulled through dispenser bore 29 when the handle and dispensing portions are rotatably arranged in this configuration. By simply rotating the handle and dispensing portions by about a half a turn or 50 in the reverse direction, a floss releasing configuration can be achieved permitting the withdrawal of floss from the tip portion. Notably, in order to enhance the gripping action of the engaging and bottom wall surfaces, knurling can be formed on each of these surfaces during manufacture.

As illustrated in FIG. 4, the second embodiment of the dental flossing device 1" comprises dispensing and handle portions 2" and 3", having essentially all of the external structural features of device 1 shown in FIG. 1. However, the view in FIG. 4 reveals that dental flossing device 1" also has a number of internal structural details not shown in FIG. 1.

In particular, handle portion 2" has hollow cavity 40 for containing a supply of dental floss 41, and also a passageway 42 formed in front end 4". As shown, passageway 42 is in communication with hollow cavity 40 in order to permit passage of dental floss 17 from hollow cavity 40, through passageway 42, aand into recess 43 formed in the front end of the handle portion. As illustrated, front end recess 43 has a semispherical bottom wall surface 44 through which passageway 42 passes. As shown, front end recess 43 also has a cylindrical side wall surface 45. For reasons which will be explained below, cylindrical side wall surface 45 has a pair of diametrically arranged, longitudinally extending grooves 46A and 46B, each being in communication with a respective cam groove 47A, 47B.

Floss dispensing portion has a base portion 9" which gradually extends into cylindrically shaped elongated portion 10, which extends into tip portion 12 in a manner similarly described in connection with the first embodiment of the invention. As shown, base portion 9" has a cylindrical side wall surface 50 which extends into a semispherical end surface 51 that is adapted for receipt within semispherical bottom wall surface 44 of the front end recess of handle portion 2". While both tip portion 12 and elongated portion 10 have a dispenser bore 52 continuously extending therethrough and along the longitudinal axis of base portion 9", dispenser bore 52 adjacent semispherical end surface 51, deflects away from the longitudinal axis and exits from a side of the semisperical end surface, as shown in FIG. 5.

As illustrated in FIG. 4, cylindrical side wall surface 50 has a pair of diametrically arranged projections 53A and 53B which are adapted for slidable receipt within grooves 46A and 46B when the dispensing portion is slid down and rotated within the front end recess of the handle portion. In this floss locking configuration, dental floss 17 passing through passageway 42 and dispenser bore 52 is securely engaged between a portion of semispherical end surface 51 and a portion of semispherical bottom wall surface 44. Consequently, the floss is internally restrained from being pulled through dispenser bore 52 when the handle and dispensing portions are rotatably arranged in this configuration. By simply rotating the handle and dispensing portions by about a quarter turn or so in the reverse direction, a floss releasing configuration can be achieved permitting withdrawal of floss from the tip portion. Notably, in order to enhance the gripping action of the semispherical surfaces 44 and 45, knurling can be formed on of these surfaces during manufacturing.

Having described the structure and function of the first and second illustrative embodiments of the present invention, a method of flossing between teeth will now be described in reference to FIGS. 6 and 7 using the dental flossing device of the present invention.

The first step of the flossing method involves dispensing a selected length of fresh dental floss from the tip end 16 of the dental flossing device. This is achieved by manually rotating the dispensing and handle portions into a floss releasing portion, and then withdrawing dental floss until its length reaches cutter element 8 on the rear end of the handle portion. The handle and dispensing portions are then manually rotated into the floss locking configuration where the dispensed length of dental floss is internally restrained and thus essentially fixed at the tip end of the device. The dispensed length is then wrapped several times about either the user's index finger (when flossing upper teeth as shown in FIG. 6) or thumb (when flossing lower teeth as shown in FIG. 7). Then, when the handle portion is grasped and encircled by the user's hand having floss wrapped about one of its fingers, the dispensed length is held taut between the tip portion of the device and the user's index finger or thumb, as shown in FIGS. 1, 6 and 7.

Figure 8:
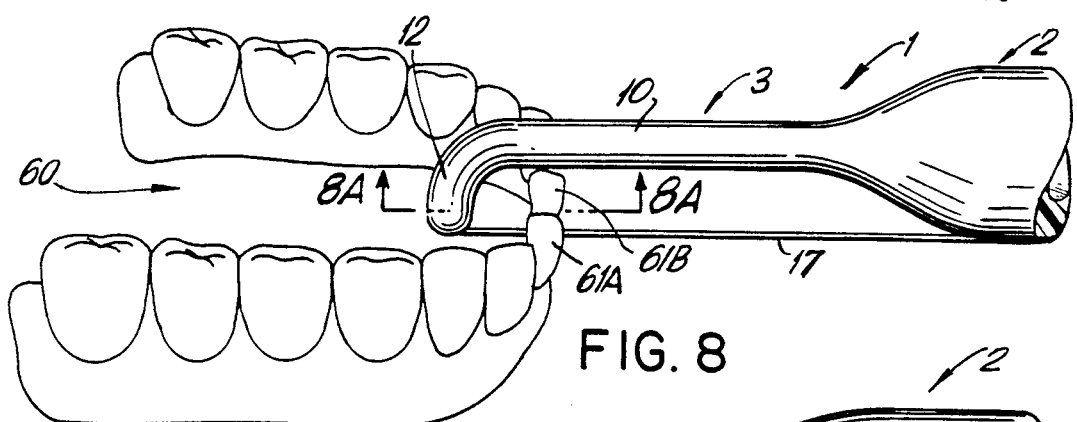
FIG. 8 is a perspective view of a set of teeth being flossed with the device of the present invention, showing the elongated portion being guided along the crown of teeth being flossed.
Figure 8A:
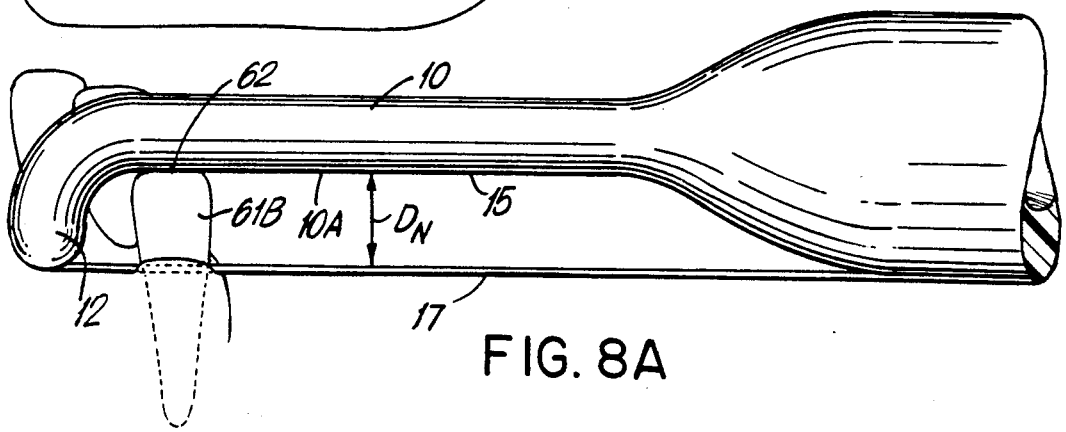
FIG. 8A is a view taken along line 8A—8A of FIG. 8, showing the crown of a tooth guiding the elongated portion of the flossing device hereof, with the tautly held floss being automatically limited to a desired depth below the gumline.

While grasping the handle portion of the device and tautly holding the dental floss as described above, tip portion 12 is inserted into the oral cavity 60 behind the user's teeth and then positioned between a pair of teeth 61A, 61B to be flossed, as shown in FIGS. 6 through 8. Then while positioning the tautly held dental floss between the pair of teeth, the handle portion is manipulated in order to move the taut dental floss about the pair of teeth, loosening food particles, plaque and the like.

Owing to the mechanical advantage of the longitudinal extent of the dental flossing device, tautly held dental floss 17 can be used to effectively floss teeth using in very simple hand maneuvering operations characteristic, in some respects, to those involved in brushing teeth. Moreover, the perpendicular-like bend which couples the tip and elongated portions of the device, permits flossing of teeth using tautly held floss immediately adjacent the tip portion, as illustrated in FIGS. 8 and 8A. This translates into a significant result, namely, requiring minimal introduction of the dispensing portion into the user's mouth, in order to floss teeth using the flossing device of the present invention.

In addition, the geometrical configuration of the tip portion provides a natural means for safety stopping further introduction of the dispensing portion into the oral cavity, if and when the tip portion is inadvertently advanced to an extreme position therewithin. The rectilinear nature of the elongated portion of the floss dispensing portion, in combination with the effective width of the tip portion, permits the user to guide the movement of the dispensing portion into the oral cavity by letting the inside surface 10A of the elongated portion 10 to side along the crown 62 of the teeth 3 being flossed, as illustrated in FIGS. 8 and 8A. At the same time, the effective width of the tip portion $W_{eff}$ and normal distance $D_N$, will limit the depth that dental floss is permitted to extend beneath the gumline to a desired level, during flossing.

Having described two illustrated embodiments of the present invention, several apparent modification come to mind. In particular, while the elongated dispensing portion of the illustrated devices has been essentially rectilinear along its entire length, it is expected that deviation from this preferred geometry, particularly adjacent the base portion, will occur in other embodiments without departing from the scope or spirit of the various aspects of the present invention.

While the particular embodiments shown and described above have proven to be useful in many applications in the dental floss dispensing and holding art, further modifications of the present invention herein disclosed will occur to persons with ordinary skill in the art. All such modifications are deemed to be within the scope and spirit of the present invention defined by the appended claims.

What is claimed is:

1. A hand-holdable device for dispensing and supporting a selected length of dispensed dental floss for use in an operational position with in an oral cavity, said hand-holdable device comprising:

a handle portion having a front end and a rear end and an elongated gripping surface extending therebetween for encirclement within a user's hand, said handle portion further having a hollow cavity for containing a supply of dental floss, and a passageway formed in said front end and in communication with said hollow cavity to permit passage of dental floss from said hollow cavity out through said passageway;

a dispensing portion having a base portion operably associated with an elongated portion extending in an essentially linear direction and terminating in a tip portion which deflects away from said linear direction, said base portion, elongated portion and tip portion having a continuously extending dispenser bore formed therethrough which permits dental floss to slidably pass from said passageway through said base portion and said elongated portion and exit from said tip portion, said dispensing portion being manually rotatable relative to said handle portion for arrangement into a floss release configuration and a floss locking configuration, wherein a selected length of dental floss is permitted to be pulled through said dispenser bore and dispensed from said tip portion when said handle portion and said dispenser portion are rotatably arranged into said floss releasing configuration, and said selected length of dispensed dental floss is locked and restrained from being pulled through said dispenser bore when said handle portion and said dispensing portion are rotatably arranged into said floss locking configuration;

a floss engaging element disposed between said base portion and at least a portion of said cylindrical recess so that said floss passing through said passageway and said dispenser bore is engaged between said flossing engaging element and at least a portion of said base portion, and also between said flossing engaging element and at least a portion of said cylindrical recess, so that said floss is restrained from being pulled through said dispenser bore when said handle portion and said dispensing portion are rotatably arranged into said floss locking configuration;

wherein said dispensing portion is operationally connectable to said handle portion by first and second threads associated with said base portion and said front end, respectively;

wherein said base portion of said dispensing portions bears said first threads, and wherein said front end of said handle portion has a cylindrical recess bearing said second threads, said second threads being releasably engagable with said first threads when said base portion is rotated within said cylindrical recess; and wherein said floss engaging element has first and second floss engaging surfaces, and wherein at least one of said floss engaging surface bears knurling.

2. The hand-holdable device of claim 1, wherein said elongated gripping surface of said handle portion is substantially cylindrical, and the rear end of said handle portion has an access opening for replenishing the supply of said dental floss when depleted.

3. The hand-holdable device of claim 2, wherein said access opening in said rear end is adapted for receipt of an end cap having floss cutting means for cutting a selected length of dispensed dental floss.

4. A method of flossing between pairs of teeth using a hand-holdable device for dispensing and supporting a selected length of dispensed dental floss in an oral cavity, said method comprising the steps of:

(a) providing a hand-holdable device having a handle portion releasably connected to a dispensing portion, said handle portion having a front end and a rear end and an elongated gripping surface extending therebetween for encirclement within a user's hand, said handle portion further having a hollow cavity for containing a supply of dental floss, and a passageway formed in said front end and in communication with said hollow cavity to permit passage of dental floss from said hollow cavity out through said passageway, said dispensing portion being releasably connected to said front end of said handle portion and having a base portion operably associated with an elongated portion extending in an essentially linear direction and terminating in a tip portion which deflects away from said linear direction, said base portion, elongated portion and tip portion having a continuously extending dispenser bore formed therethrough which permits dental floss to slidably pass from said passageway through said dispenser bore and exit from said tip portion, said dispensing portion being manually rotatable relative to said handle portion for arrangement into a floss releasing configuration and a floss locking configuration, wherein a selected length of dental floss is permitted to be pulled through said dispenser bore and dispensed from said tip portion when said handle portion and said dispenser portion are rotatably arranged into said floss releasing configuration, and said selected length of dispensed dental floss is locked and restrained from being pulled through said dispenser bore when said handle portion and said dispensing portion are rotatably arranged into said floss locking configuration;

(b) with said dispensing and handle portions arranged in said floss releasing configuration, dispensing a selected length of dental floss from said tip portion, said selected length being extendable from at least said tip portion to said rear end of said handle portion;

(c) with said dispensing and handle portions arranged in said floss locking configuration, wrapping the free end of the dispensed length of dental floss about either the index finger or thumb of the user's hand a sufficient number of times, so that when said handle portion is grasped and encircled by said hand, said dispensed length of dental floss is held taut between said tip portion and said index finger or thumb;

(d) while grasping said handle portion and holding said dental floss as recited in step (c), inserting said tip portion into said oral cavity behind said teeth, and positioning said tautly held dental floss between a pair of teeth to be flossed; and (e) while positioning said tautly held dental floss between said pair of teeth as recited in step (d), manipulating said handle portion so as to move said tautly held dental floss between said pair of teeth.

* * * * *